United States Patent
Daniels et al.

(10) Patent No.: US 8,741,117 B2
(45) Date of Patent: Jun. 3, 2014

(54) DEVICE AND METHOD FOR DETECTING REDOX REACTIONS IN SOLUTION

(71) Applicants: Jonathan S. Daniels, Palo Alto, CA (US); Oguz H. Elibol, Sunnyvale, CA (US); Grace M. Credo, San Mateo, CA (US); Xing Su, Cupertino, CA (US)

(72) Inventors: Jonathan S. Daniels, Palo Alto, CA (US); Oguz H. Elibol, Sunnyvale, CA (US); Grace M. Credo, San Mateo, CA (US); Xing Su, Cupertino, CA (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 13/628,728

(22) Filed: Sep. 27, 2012

(65) Prior Publication Data

US 2014/0083871 A1 Mar. 27, 2014

(51) Int. Cl.
*G01N 27/26* (2006.01)

(52) U.S. Cl.
USPC ........ 204/400; 435/287.1; 435/6.1; 422/68.1; 422/82.01; 324/686; 204/403.01

(58) Field of Classification Search
USPC ................ 204/400–450; 435/287.1, 287.2, 6; 324/658–667; 422/82.01, 68.1
See application file for complete search history.

(56) References Cited

U.S. PATENT DOCUMENTS

| | | | |
|---|---|---|---|
| 4,168,442 A * | 9/1979 | Satou et al. | 327/310 |
| 7,172,922 B2 | 2/2007 | Benjamin et al. | |
| 7,304,674 B2 | 12/2007 | Mentzer et al. | |
| 7,342,212 B2 | 3/2008 | Mentzer et al. | |
| 8,093,636 B2 | 1/2012 | Park | |
| 2003/0022150 A1* | 1/2003 | Sampson et al. | 435/4 |
| 2010/0221846 A1* | 9/2010 | Widdershoven | 436/512 |
| 2010/0300899 A1* | 12/2010 | Levine et al. | 205/792 |
| 2011/0065588 A1* | 3/2011 | Su et al. | 506/2 |

OTHER PUBLICATIONS

Anderson et al. (12MTC 2008, IEEE Conf., May 2008).*
Daniels et al. (Electroanalysis 19, 2007, No. 12, 1239-1257).*
Anderson et al. (Journal of Stellar EE315 Circuits).*
Anderson et al. (IEEE Transactions on Circuits and Systems-I: Regular Papers, vol. 55, No. 11, Dec. 2008).*
Daniels (Thesis, Mar. 2010).*
Prakash et al. (IEEE Sensors Journal, vol. 7, No. 3, 2007).*
Abbas El Gamal et al., "CMOS Image Sensors", IEEE Circuits & Devices Magazine, May/Jun. 2005, pp. 6-20.

* cited by examiner

*Primary Examiner* — Jennifer Dieterle
(74) *Attorney, Agent, or Firm* — Pillsbury Winthrop Shaw Puttman LLP

(57) ABSTRACT

Described herein is a device comprising a plurality of first reaction electrodes arranged in an array, the plurality of first reaction electrodes configured to be exposed to a solution and having a capacitance; first circuitry configured to controllably connect the plurality of first reaction electrodes to a bias source and controllably disconnect the plurality of first reaction electrodes from the bias source; and second circuitry configured to measure a rate of charging or discharging of the capacitance. Also described herein is a method of using this device to sequence DNA.

26 Claims, 11 Drawing Sheets

DEVICE AND METHOD FOR DETECTING REDOX REACTIONS IN SOLUTION

CROSS-REFERENCE TO RELATED APPLICATIONS

Reference is made to commonly owned and co-pending U.S. application Ser. No. 12/655,578 titled "Nanogap Chemical and Biochemical Sensors," filed Dec. 31, 2009, now pending; U.S. patent application Ser. No. 11/226,696, titled "Sensor Arrays and Nucleic Acid Sequencing Applications," filed Sep. 13, 2005, now pending; which is a continuation-in-part application that claims the benefit of U.S. patent application Ser. No. 11/073,160, titled "Sensor Arrays and Nucleic Acid Sequencing Applications," filed Mar. 4, 2005; U.S. patent application Ser. No. 11/967,600, titled "Electronic Sensing for Nucleic Acid Sequencing," filed Dec. 31, 2007 now pending; U.S. patent application Ser. No. 12/319,168, titled "Nucleic Acid Sequencing and Electronic Detection," filed Dec. 31, 2008, now pending; U.S. patent application Ser. No. 12/459,309, titled "Chemically Induced Optical Signals and DNA Sequencing," filed Jun. 30, 2009, now pending; U.S. patent application Ser. No. 12/655,459, titled "Solid-Phase Chelators and Electronic Biosensors," filed Dec. 30, 2009, now pending; U.S. patent application Ser. No. 12/823,995, titled "Nucleotides and Oligonucleotides for Nucleic Acid Sequencing," filed Jun. 25, 2010, now pending; U.S. patent application Ser. No. 12/860,462, titled "Nucleic Acid Sequencing," filed Aug. 20, 2010, now pending; the disclosures of which are incorporated herein by reference in their entirety. Appropriate components for device/system/method/process aspects of the each of the foregoing U.S. patents and patent publications may be selected for the present disclosure in embodiments thereof.

BACKGROUND

DNA sequencing is the process of reading the nucleotide bases in a DNA molecule. It includes any method or technology that is used to determine the order of the four bases—adenine, guanine, cytosine, and thymine—in a strand of DNA.

Knowledge of DNA sequences is useful for basic biological research, and in numerous applied fields such as diagnostic, biotechnology, forensic biology, and biological systematics. The advent of DNA sequencing has accelerated biological research and discovery. The rapid speed of sequencing attained with modern DNA sequencing technology has been instrumental in the sequencing of the human genome, in the Human Genome Project. Related projects, often by scientific collaboration across continents, have generated the complete DNA sequences of many animal, plant, and microbial genomes.

New development in the medical field (e.g., personalized medicine) and basic biological research (e.g., animal or plant genome projects) calls for rapid sequencing of large number (e.g., above 10,000) of DNA fragments in a practical period of time (e.g., several hours to several days), which is usually referred to as a high-throughput sequencing. Traditional chemistry-based and optic-based DNA sequencing methods such as the Maxam—Gilbert method and Chain-termination methods suffer from their requirements of complex sample preparation and slow rate of base detection, and are generally unsuitable in these applications.

Exemplar high-throughput sequencing techniques include Massively Parallel Signature Sequencing (MPSS) developed by Lynx Therapeutics, Polony sequencing developed by Prof. George Church at Harvard University, parallelized pyrosequencing developed by 454 Life Sciences (now Roche Diagnostics), SOLiD sequencing developed by Applied Biosystems (now Life Technologies), pH-based semiconductor sequencing developed by Ion Torrent (now Life Technologies), nanopore sequencing, etc.

SUMMARY

Described herein is a device comprising: a plurality of first reaction electrodes arranged in an array, the plurality of first reaction electrodes configured to be exposed to a solution and having a capacitance; first circuitry configured to controllably connect the plurality of first reaction electrodes to a bias source and controllably disconnect the plurality of first reaction electrodes from the bias source; and second circuitry configured to measure a rate of charging or discharging of the capacitance of the plurality of first reaction electrodes.

Also described herein is a method comprising contacting an electrode to a solution comprising one or more analyte; connecting the electrode to a bias source such that a voltage of the electrode is substantially at a voltage of the bias source; disconnecting the electrode from the bias source; measuring change of the voltage of the electrode.

Further described herein is a method comprising contacting a plurality of electrodes to a solution, each of the plurality of electrodes having a DNA molecule attached thereto or in proximity thereof, wherein DNA molecule has a primer hybridized thereto; adding at least one type of nucleoside triphosphate to the solution; setting the solution to a temperature suitable for the at least one type of nucleoside triphosphate to be incorporated into at least some of the primers; measuring a rate of charge or discharge of capacitance of each of the plurality of electrodes. Incorporating the at least one type of nucleoside triphosphate can release a reaction product that undergoes a redox reaction at the electrodes. The redox reaction may cause charging or discharging of the capacitance. The nucleoside triphosphate may be in its natural form or modified with a moiety which is either directly redox-active upon release or can be subsequently activated.

DETAILED DESCRIPTION

A DNA molecule may be sequenced by detecting reaction products from incorporation of individual nucleotides into a polynucleotide chain complementary to the DNA molecule or cleavage of individual nucleotides from the DNA molecule. Various enzymes (e.g., polymerase, deoxyribonuclease) may be used to facilitate the incorporation or cleavage.

One method to detect these reaction products is electrochemistry. Electrochemistry is a branch of chemistry that studies chemical reactions which take place in a solution at the interface of an electron conductor (a metal or a semiconductor) and an ionic conductor (the electrolyte), and which involve electron transfer between the electrode and the electrolyte or species in solution. When the reaction products undergo redox reactions in an electrochemistry cell, electrical signatures (e.g., cyclic voltammogram) of the reaction products may be used to identify them. For example, the reaction products may be those released from incorporation of chemically-modified nucleotides into DNA, as described in U.S. patent application Ser. No. 11/967,600, titled "Electronic Sensing for Nucleic Acid Sequencing," which is hereby incorporated by reference in its entirety.

Figure 1:
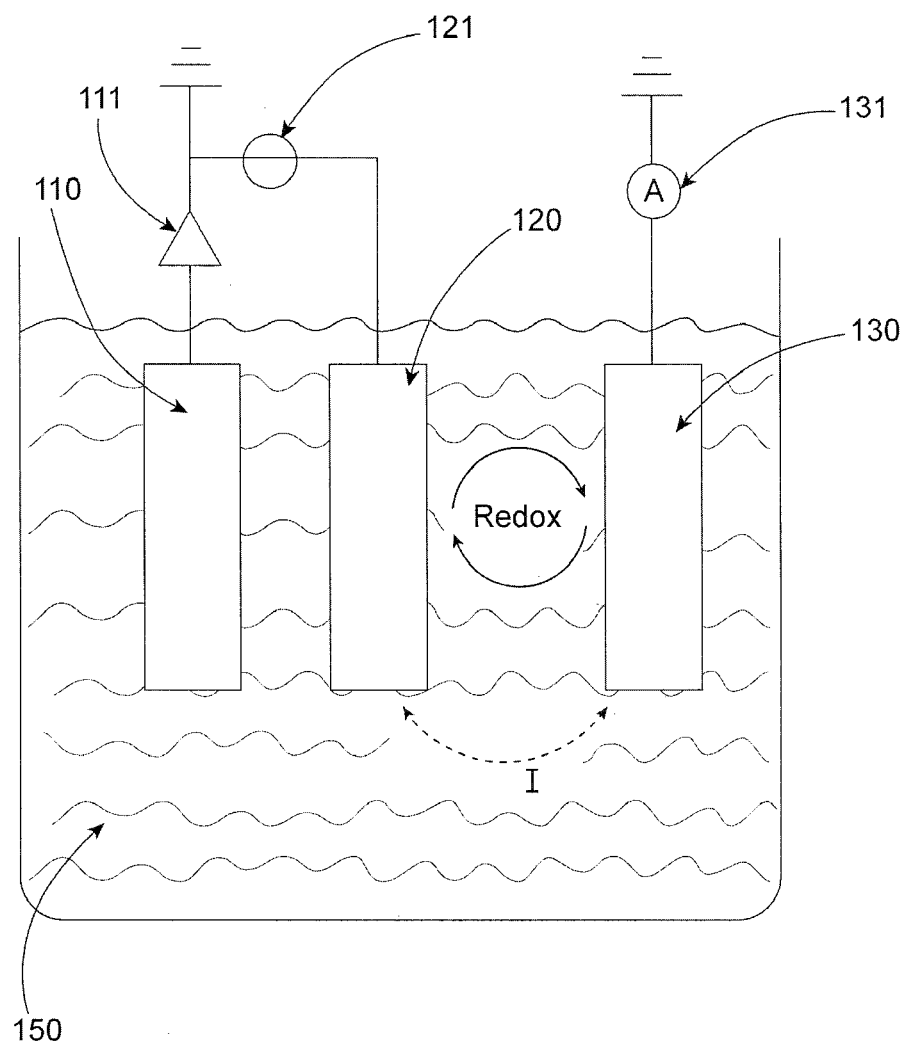
FIG. 1 shows an exemplary three-electrode electrochemistry cell.

FIG. 1 shows an exemplary three-electrode electrochemistry cell: a reference electrode 110, a second reaction electrode 120 and a first reaction electrode 130 in a solution (electrolyte) 150. The electrochemistry cell can be used to conduct various electrochemical reactions. One kind electrochemical reaction is called voltammetry. In voltammetry, information about an analyte can be obtained by measuring the current through the first reaction electrode 130 and/or the current through the second reaction electrode 120. The reference electrode 110 is a half cell with a fixed reduction potential to the solution. The reference electrode 110 may act as reference in measuring and controlling the potential on the second reaction electrode 120. The reference electrode 110 is usually connected to electrical ground through a high impedance (e.g., an unity gain op amp 111). Electrical current through the reference electrode 110 is negligible. The reference electrode 110 suitable in a aqueous electrolyte may be, for example, standard hydrogen electrode (SHE), normal hydrogen electrode (NNE), reversible hydrogen electrode (RHE), saturated calomel electrode (SCE), copper-copper(II) sulfate electrode (CSE), silver-silver chloride (Ag/AgCI) electrode, etc. The reference electrode 110 may also be a pseudoreference or quasireference electrode (QRE) which is less stable and less reproducible in the electrode-solution potential but sufficient for the measurement. The second reaction electrode 120 is electrically biased relative to the reference electrode 110. The second reaction electrode 120 may be biased using any suitable electrical circuitry 121. The bias on the second reaction electrode 120 may be used to control the voltage of the solution 150 relative to the voltage of the first reaction electrode 130. In this case the second electrode 120 is called an auxiliary or counter electrode and controls the potential of the solution. In some situations, the function of electrodes 110 and 120 can be combined into a single electrode. The electrical bias on the second reaction electrode 120 may be fixed or varied during electrochemical reactions. The second reaction electrode 120 is an electrically conducting material such as metal or semiconductor. For instance, the second reaction electrode 120 may comprise platinum, gold, doped diamond, glassy carbon, indium tin oxide, or a combination thereof. Furthermore, the second reaction electrode 120 may be coated with an organic or inorganic film to improve its electrochemical properties. The second reaction electrode 120 may be inert (i.e., not reactive with the electrolyte or analyte) or reactive. The first reaction electrode 130 passes electrical current needed to balance the current observed at the second reaction electrode 120. The electrical current through the first reaction electrode 130 may be measured using any suitable electrical circuitry 131. The first reaction electrode 130 can be any electrically conducting material but preferably is not dissolved into the electrolyte during electrochemical reactions. For instance, the first reaction electrode 130 may comprise platinum, gold, doped diamond, glassy carbon, indium tin oxide, or a combination thereof. Furthermore, the first reaction electrode 130 may be coated with an organic or inorganic film to improve its electrochemical properties.

The second reaction electrode 120 need not be used as a traditional counter electrode (with potential set by electronic feedback to control the solution voltage). A voltage applied to the second reaction electrode 120 may be used to initiate redox reaction cycles between the second reaction electrode 120 and the first reaction electrode 130. Preferably, electrodes 120 and 130 are in very close proximity, e.g. with 50 nm from each other. Namely, a chemical species receives one or more electrons (i.e., reduced) at the second reaction electrode 120, diffuses to the first reaction electrode 130, loses one or more electrons (i.e., oxidized) at the first reaction electrode 130 and diffuses back to the second reaction electrode 120; or a chemical species receives one or more electrons (i.e., reduced) at the first reaction electrode 130, diffuses to the second reaction electrode 120, loses one or more electrons (i.e., oxidized) at the second reaction electrode 120 and diffuses back to the first reaction electrode 130. The redox cycle may be used to increase the current through the first reaction electrode 130 and/or the second reaction electrode 120 to facilitate measurement of this current.

The electrochemistry cell may have more than three electrodes. The electrical current through each electrode may be measured independently. The electrical current on each electrode yields information about redox reaction in the vicinity of that electrode.

In certain situations, for example, high reaction potentials of the analyte, unfavorable voltage on the working electrode, low concentration of the analyte, etc. may cause the electrical current though one of the electrodes to be very small. Small electrical current may be difficult to measure reliably, especially in a solution environment, where noise tends to be high. Small electrical currents on spatially proximate electrodes may be especially challenging to measure.

Figure 2A:
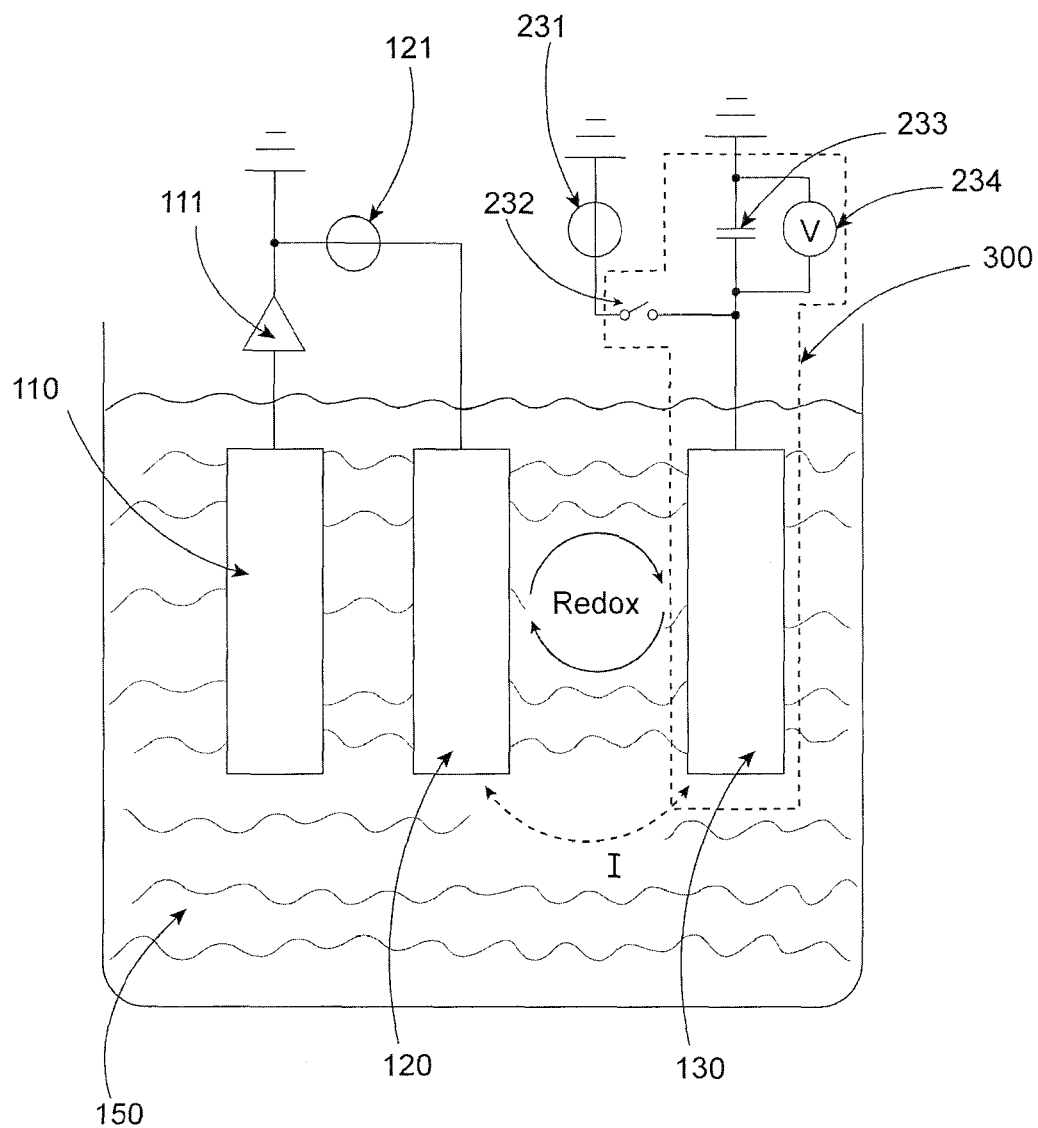
FIG. 2A shows an exemplary three-electrode electrochemistry cell according to an embodiment, wherein electrical current through one of the electrodes is measured by measuring the rate of charging or discharging of capacitance of that electrode.

According to an embodiment shown in FIG. 2A, electrical current through an electrode may be measured by measuring the rate of charging or discharging of capacitance of that electrode. For example, electrical current through the first reaction electrode 130 may be measured by measuring the rate of charging or discharging of capacitance 233 of the first reaction electrode 130. Although the capacitance 233 of the first reaction electrode 130 is depicted in FIG. 2A as a capacitor separate from the capacitance, it need not comprise a physical capacitor component, but a combination of self-capacitance of the first reaction electrode 130 and capacitance of the interface between the first reaction electrode 130 and the solution 150.

Figure 2B:
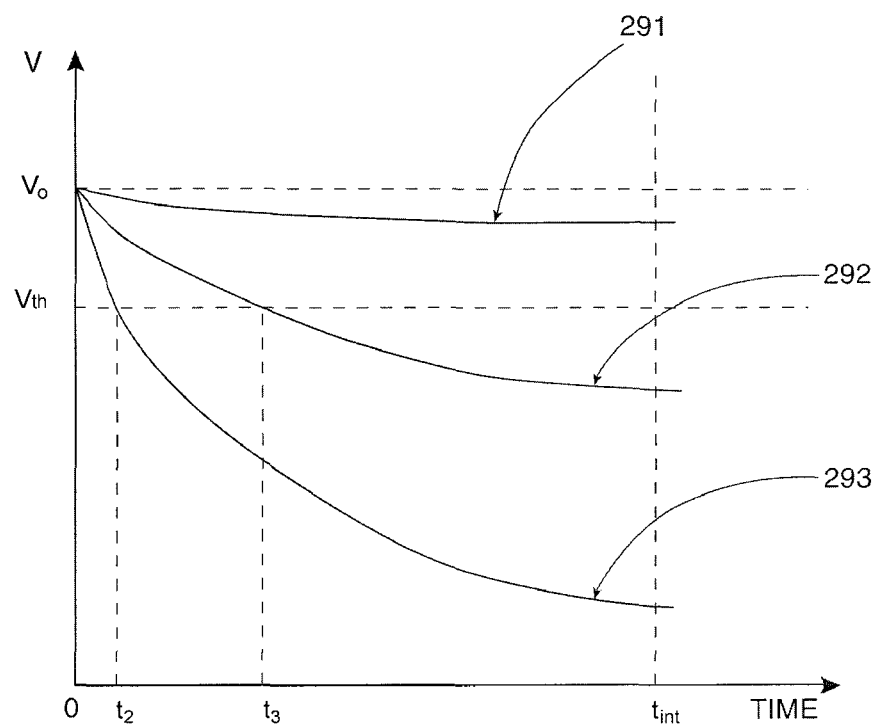
FIG. 2B shows an exemplary graph of the voltage of one of the three electrodes as a function of time, when the redox reaction discharges the capacitance of that electrode.

The circuitry connected to the first reaction electrode 130 as depicted in FIG. 2A is one example that can be used to measuring the rate of charging or discharging of the capacitance 233. In an embodiment, switch 232 is closed to connect the first reaction electrode 130 to a bias source 231. At this state, the voltage on the first reaction electrode 130 is at the voltage of the bias source 231, denoted as $V_0$. The switch 232 may be any circuitry that can electrically connect and disconnect the first reaction electrode 130 to the bias source 231. For example, the switch 232 may be a toggle switch, a relay or a transistor. After the switch 232 is opened to disconnect the first reaction electrode 130 from the bias source 231, redox reactions (electron transfer between the electrode and a chemical species in the solution) occurring at the first reaction electrode 130 start to charge or discharge the capacitance 233 and as a result the voltage of the first reaction electrode 130 deviates from $V_0$. The rate of charging and discharging of the capacitance 223 can be derived from the change of the voltage of the first reaction electrode 130. The voltage of the first reaction electrode 130 may be measured using any suitable circuitry 234. Circuitry 234 is not limited to a voltmeter. In an embodiment, the circuitry 234 may comprise A/D converter. In an embodiment, the circuitry 234 may comprise a buffer. The buffer may drive an A/D converter shared with other electrodes. FIG. 2B shows an exemplary graph of the voltage of the first reaction electrode 130 as a function of time, when the redox reaction discharges the capacitance 233. The more molecules undergo redox reactions in the vicinity of the first reaction electrode 130, the greater the rate of charging or discharging of the capacitance 233. For example, trace 291 in FIG. 2B shows discharge of the capacitance 233 when essentially no molecules undergo redox reactions in the vicinity of the first reaction electrode 130. The slight drop of the voltage on the first reaction electrode 130 is due to leakage current through the solution 150 and/or leakage current from the circuitry 231 and/or 234. Traces 292 and 293 in FIG. 2B show discharge of the capacitance 233 when some molecules undergo redox reactions in the vicinity of the first reaction electrode 130. Trace 293 shows a greater rate of discharge that trace 292 because more molecules undergo redox reactions in the vicinity of the first reaction electrode 130 when trace 293 is recorded than when trace 292 is recorded. The rate of discharge may be measured directly (e.g., the slope of the traces in FIG. 2B) or by any other suitable techniques. For example, the rate of discharge may be measured by the amount of voltage change from $V_0$ at a time point $t_{int}$ after the first reaction electrode 130 disconnects from the bias source 231. In alternative, to reduce drift or noise in circuitry 234, switch 232 can be closed at a time just after $t_{int}$, resetting the voltage of the first reaction electrode 130 to $V_0$, and the rate of discharge may be measured by the difference between the voltage at $t_{int}$ and the voltage after the reset. In another alternative, the rate of discharge may be measured by the amount of time for the voltage of the first reaction electrode 130 to change from $V_0$ by a predetermined amount to a voltage $V_{th}$ after the first reaction electrode 130 disconnects from the bias source 231.

Figure 3A:
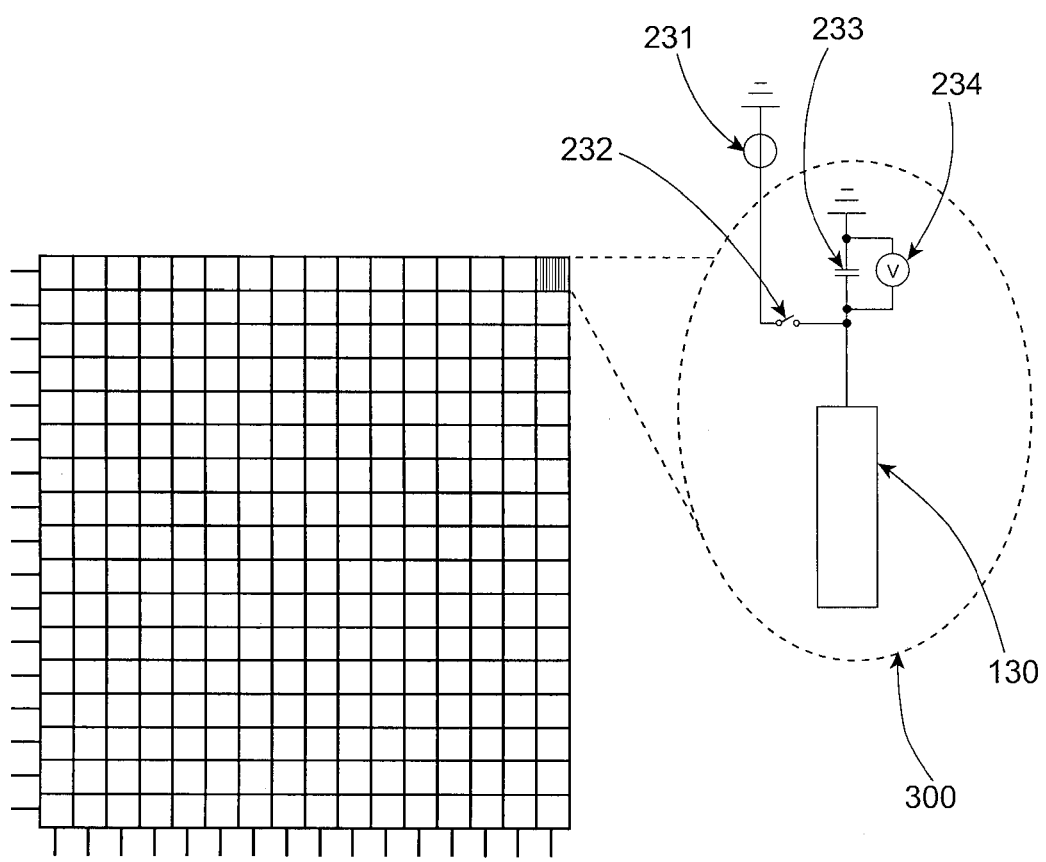
FIG. 3A shows an array of the circuitry in the dotted box 300 in FIG. 2A.
Figure 3B:
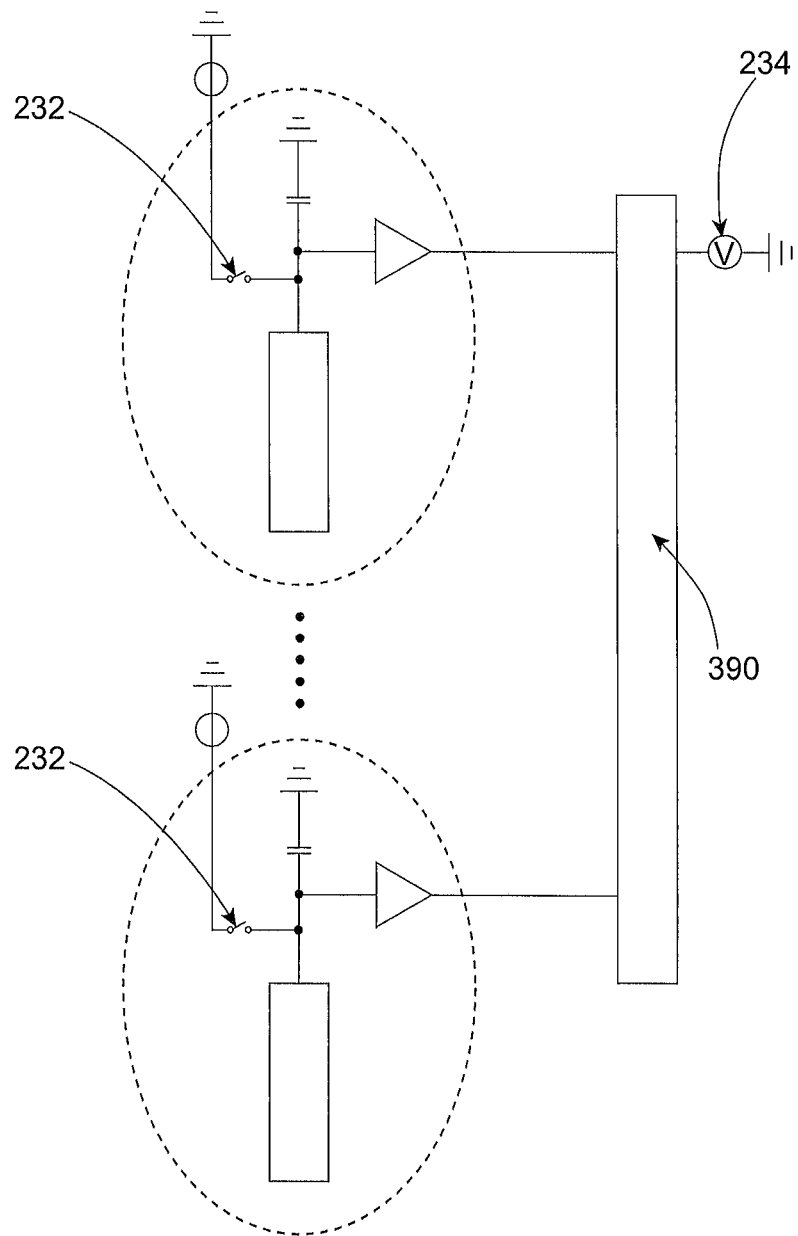
FIG. 3B shows that circuitry to measure the rate of charge or discharge of one of the electrodes may be shared in the array of FIG. 3A.

In an embodiment, the circuitry in the dotted box 300 in FIG. 2A, including the first reaction electrode 130 may be integrated in a microchip. In an embodiment, such a microchip may have a plurality of copies of the circuitry in the dotted box 300. These copies may be arranged in an array (e.g., a rectangular or hexagonal grid) such as the array shown in FIG. 3A. Preferably, the bias source 231 is shared among these copies. For the purpose of this disclosure, a copy may be referred to as a "pixel." In an embodiment as shown in FIG. 3A, a pixel may have its own circuitry 234 (i.e., not shared with other pixels) integrated in the pixel. The measurements of the circuitry 234 in each may be transmitted to a bus through a multiplexer. In an embodiment depicted in FIG. 3B, the circuitry 234 may be shared among these copies through a multiplexer 390. A multiplexer (or MUX) is a device that selects one of several analog or digital input signals and forwards the selected input into a single line. In an embodiment, the circuitry 234 includes a high-impedance buffer configured to measure the voltage of the first reaction electrode 130 without discharging the capacitance 233. In an embodiment, the high-impedance buffer is included in each pixel but other portions (such as A/D converter) of the circuitry 234 are shared among many pixels through a multiplexer. In an embodiment, a pixel comprises a memory configured to store the measurement by the circuitry 234 of the first reaction electrode 130. For example, the memory may be configured to measure and store the value of the voltage of the first reaction electrode 130 at $t_{int}$ or the time at which the voltage of the first reaction electrode 130 crossed a predetermined threshold value.

Figure 3C:
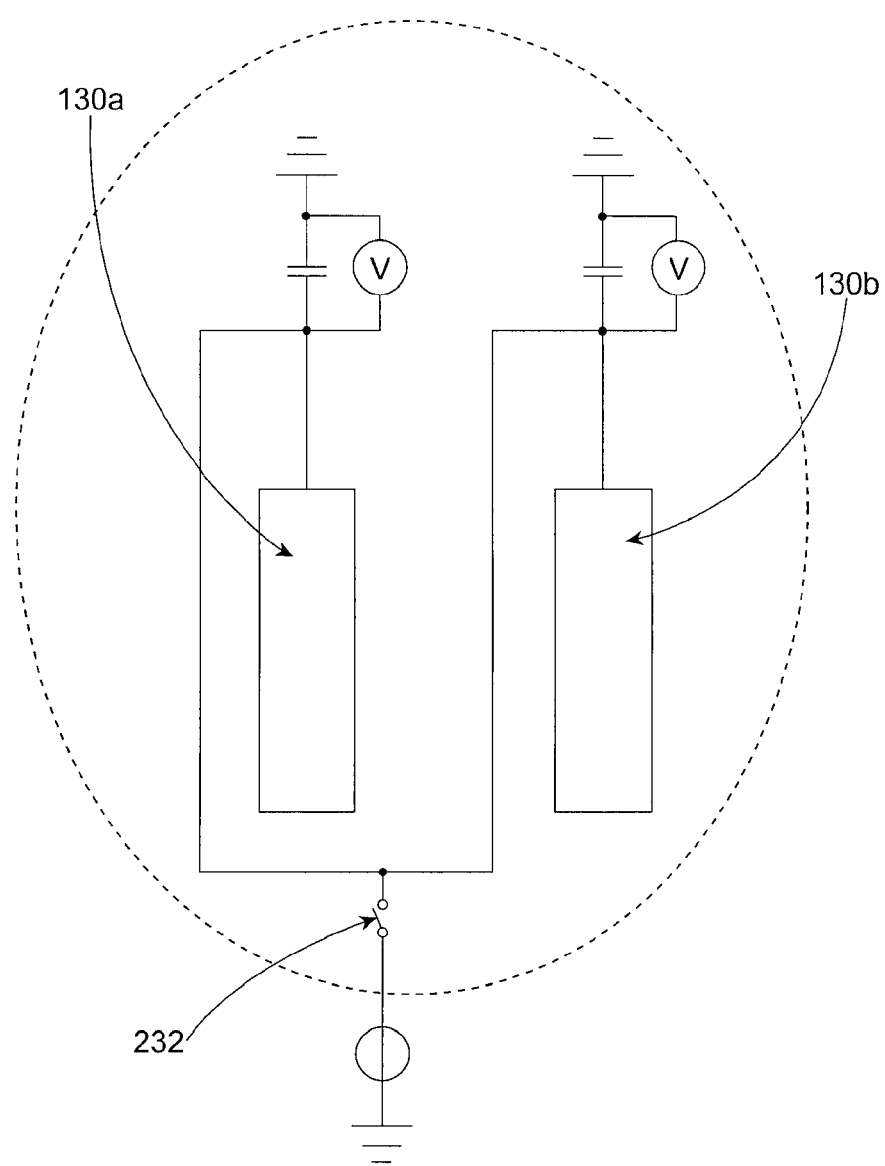
FIG. 3C shows an array of the circuitry in the dotted box 300 in FIG. 2A, except that a pixel of the array has at least two electrodes, the rate of charging or discharging of capacitance of which are measured.

In an embodiment schematically shown in FIG. 3C, a pixel may have at least two first reaction electrodes 130a and 130b. The first reaction electrodes 130a and 130b are arranged to be in vicinity of each other. As used in this disclosure, the word "vicinity" means distance no greater than the diffusion length of the analyte at $t_{int}$. Correlation of the voltages on the first reaction electrodes 130a and 130b may be used to determine the validity of data collected from this pixel. For example, if the voltages on the first reaction electrodes 130a and 130b differ by a threshold value, data collected from this pixel is considered invalid and discarded.

Figure 3D:
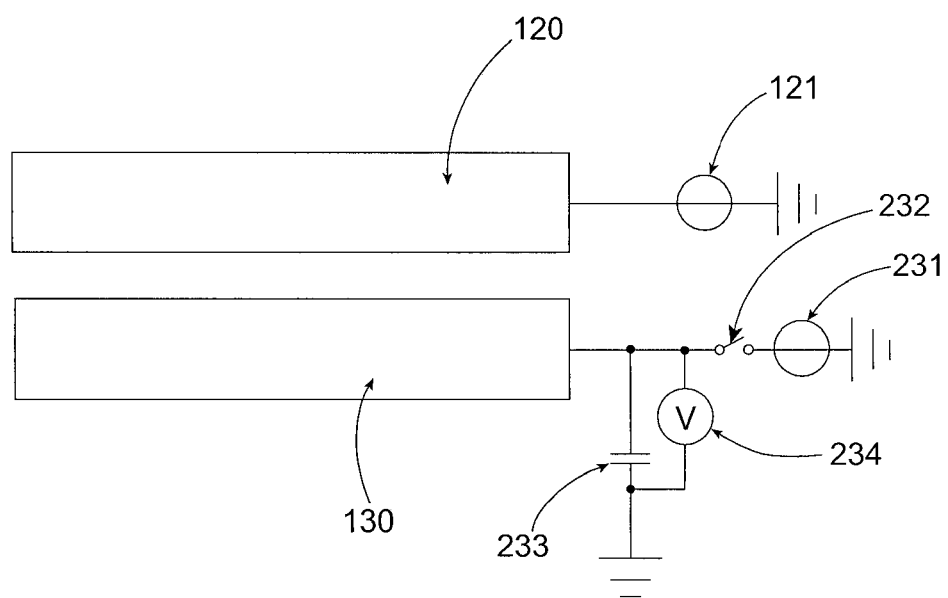
FIG. 3D shows an array of the circuitry in the dotted box 300 in FIG. 2A, except that a pixel of the array has another biased electrode integrated in the pixel.

In an embodiment schematically shown in FIG. 3D, a pixel may have the second reaction electrode 120 integrated in the pixel. In an embodiment, the second reaction electrode 120 can be shared among more than one pixel.

In an embodiment, a pixel has an area from 0.01 to 100 $\mu m^2$, such as about 1 $\mu m^2$. In one embodiment, the array has more than 100 pixels, $10^6$ pixels, or $10^{10}$ pixels. In an embodiment, the pixels do not comprise a photodiode.

Figure 4A:
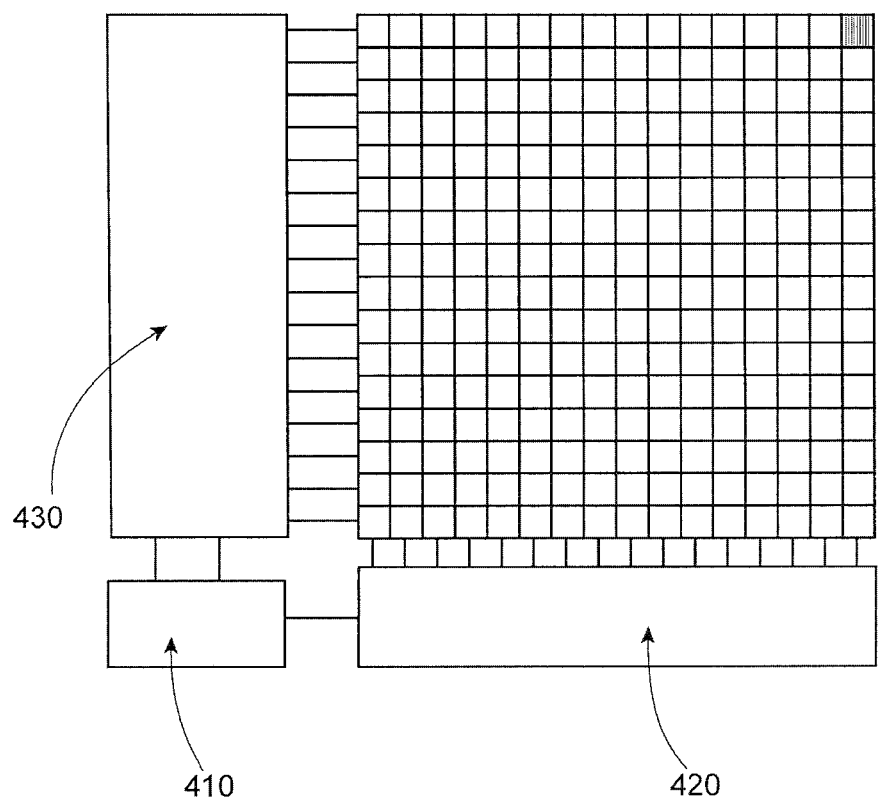
FIG. 4A shows an exemplary embodiment of the array.
Figure 4B:
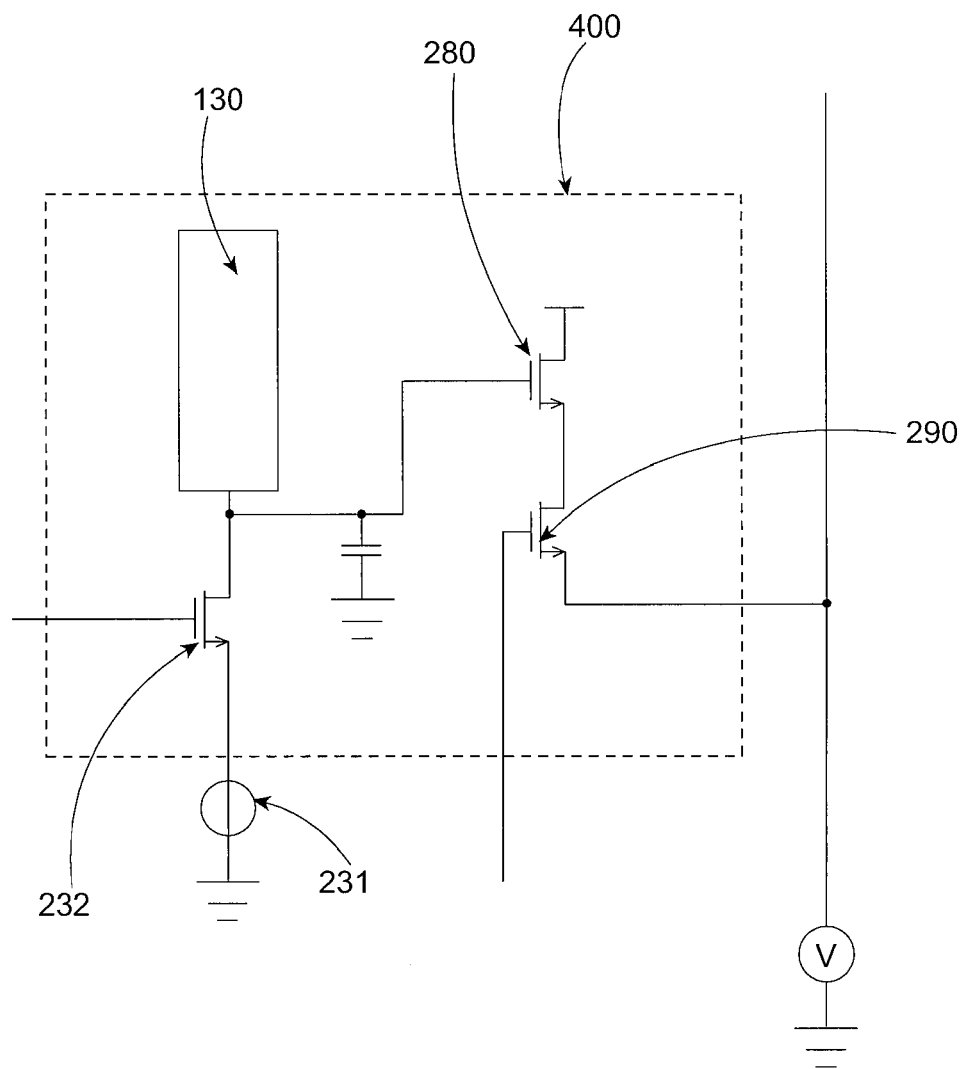
FIG. 4B shows an exemplary schematic of a pixel in the array of FIG. 4A.

FIG. 4A shows an exemplary embodiment of the array. The pixels may be interrogated by enabling a row of pixels using row decoder 430 which connects the pixels to a shared A/D converter by enabling a switch (e.g., a transistor 290 in FIG. 4B). 420 may be an array of A/D converters (one for each column of pixels) or a multiplexer that connects the column outputs to one or more shared A/D converters. 420 and 430 are under control of a controller 410. FIG. 4B shows an exemplary schematic of a pixel 400 in the array of FIG. 4A. The multiplexing functionality may be provided by transistor 290. Transistor 280 may act as a voltage buffer to read the voltage at electrode 130 without discharging the capacitance of electrode 130. Switch 232 may be implemented as a transistor. The functionality provided by switch 232, transistors 280 and 290 can be implemented using different electronic devices than shown as examples in FIG. 4B. One row of pixels in the array may be interrogated at a time, and the entire array may be interrogated by interrogating each row of pixels. Furthermore, the entire array can be interrogated multiple times to obtain the information such as that contained in FIG. 2B.

Figure 5:
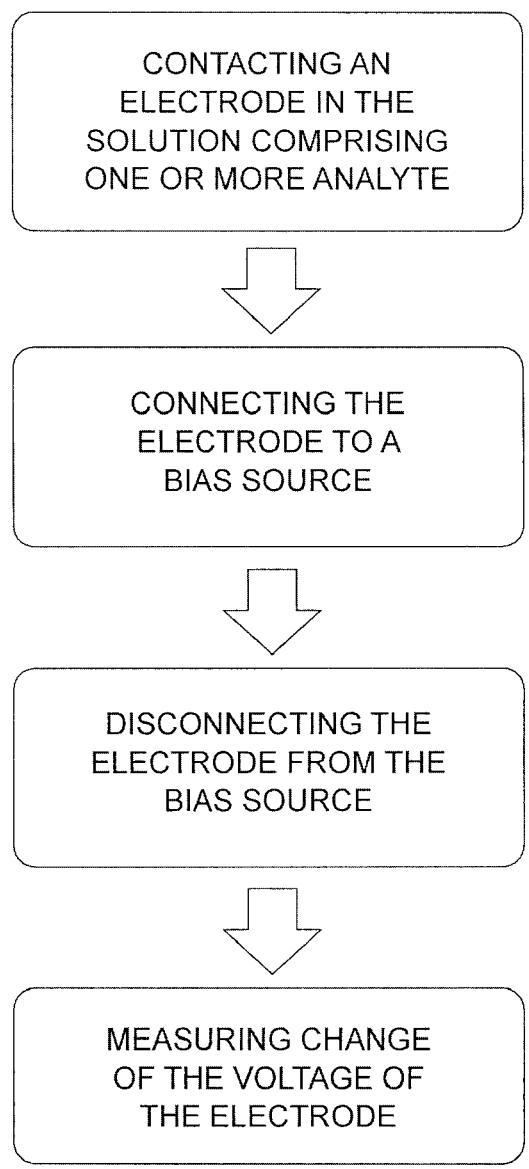
FIG. 5 shows a flowchart of a method of operating the array of FIG. 4A.

In an embodiment, as schematically shown in the flowchart of FIG. 5, a method of operating the array comprises: contacting the first reaction electrode 130 to the solution 150 comprising one or more analyte; connecting the first reaction electrode 130 to the bias source 231, such that the voltage of the first reaction electrode 130 is substantially at the voltage $V_0$ of the bias source 231; disconnecting the first reaction electrode 130 from the bias source 231; measuring change of the voltage of the first reaction electrode 130, wherein the change of the voltage is produced from charging or discharging of capacitance of the first reaction electrode 130 due to redox reactions in the vicinity of the first reaction electrode 130. The method may further comprise storing the change of the voltage of the first reaction electrode 130 in a memory.

Figure 6:
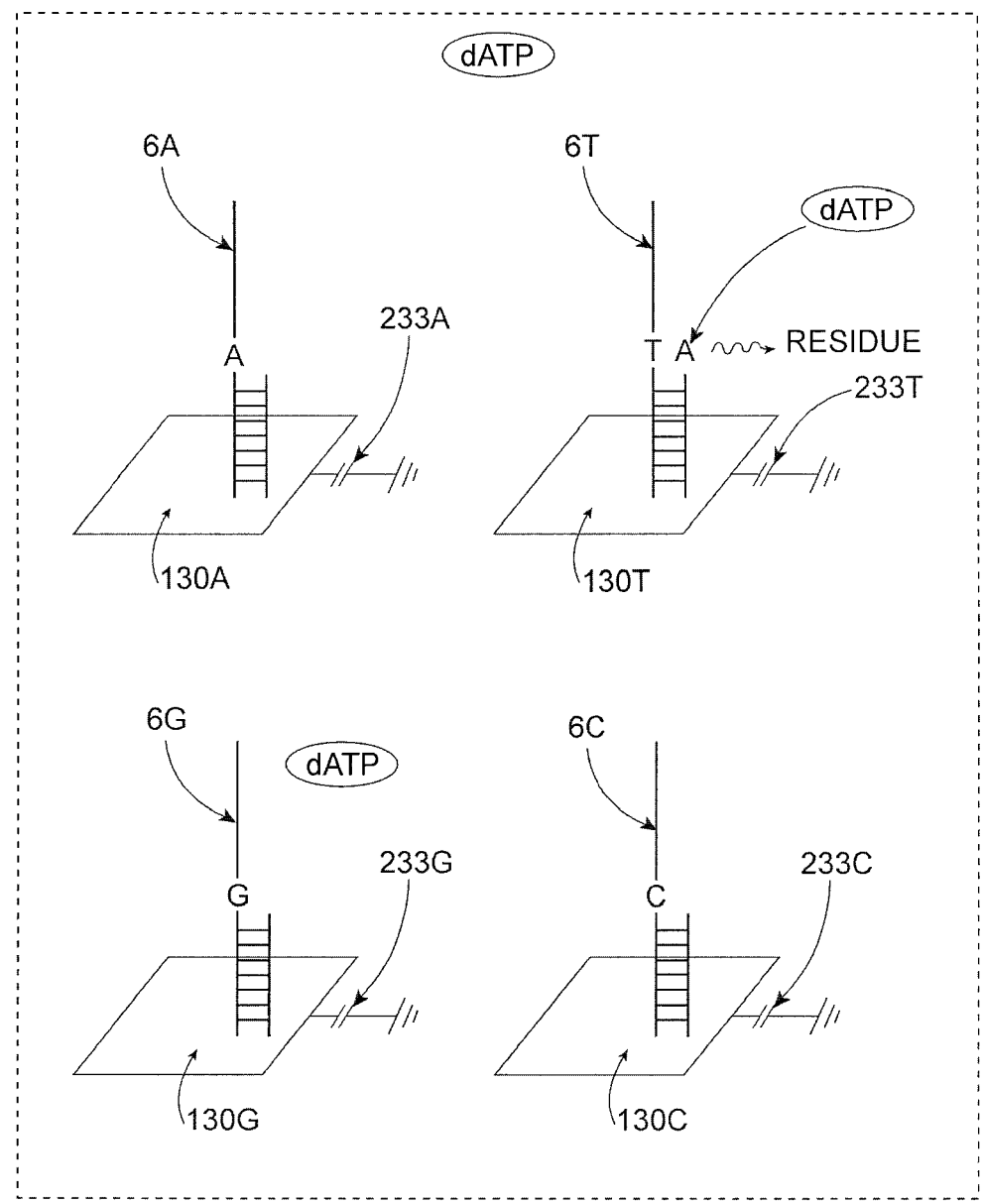
FIG. 6 shows an exemplary scheme to sequence DNA with the array of FIG. 4A.

An exemplary method of using the array to sequence DNA may comprise the following. A pixel of the array may have one or more copies of a DNA molecule to be sequenced attached to or in proximity of the first reaction electrodes 130 therein, or the second reaction electrode 120 if the pixel has its own second reaction electrode 120 (i.e., the second reaction electrode 120 not shared with other pixels), the DNA molecule to be sequenced having a primer hybridized thereto. The pixel preferably does not have DNA molecules of more than one sequence. The array is in contact with the solution 150. The solution 150 comprises reagents such as polymerase, and salt (e.g., $MgCl_2$). Only one type of nucleoside triphosphate (i.e., one type among deoxyadenosine triphosphate (dATP), deoxyguanosine triphosphate (dGTP), deoxythymidine triphosphate (dTTP) and deoxycytidine triphosphate (dCTP)) is added to the solution 150. The nucleoside triphosphate may be in its natural form or modified with a moiety that can undergo a redox reaction in the solution 150. The solution 150 is set to a temperature suitable for the polymerase to incorporate the nucleoside triphosphate into the one or more DNA primers. Only pixels with DNA molecules whose next unpaired base is complementary to the added nucleoside triphosphate will have the nucleoside triphosphate incorporated to the primers. For example, as illustrated in FIG. 6, in which dATP is added into solution 150 as the nucleoside triphosphate, four pixels each with a first reaction electrode (130A, 130T, 130G and 130C) is shown. On first reaction electrodes 130A, 130I, 130G and 130C DNA molecules 6A, 6T, 6G and 6C are respectively attached. Each of these DNA molecules has a primer being extended by the polymerase. On DNA molecules 6A, 6T, 6G and 6C, the next unpaired bases are A, T, G and C, respectively. The dATP in the solution 150 will thus only be incorporated to the primer on the DNA molecule 6A. The polymerase splits the terminal phosphate groups (with or without the moiety) from the incorporated dATP. The terminal phosphate groups split from nucleoside triphosphate is often referred to as phosphate residue. The phosphate residue and/or the moiety undergoes redox reaction in the vicinity of the first reaction electrode 130T. As a result, capacitance 233T of the first reaction electrode 130I charges or discharges at a rate beyond that caused by leakage current (e.g., trace 291 in FIG. 2B). Since no incorporation of dATP to the primers on the other three first reaction electrodes 130A, 130G and 130C, capacitance 233A, 233G and 233C of these first reaction electrodes 130A, 130G and 130C do not charges or discharges at a rate beyond that caused by leakage current. The difference between the rate of charge of discharge on the first reaction electrodes 130A, 130T, 130G and 130C indicates that the next unpaired base on DNA 6T is thymine. Solution 150 is removed and the array is washed to remove any residue of solution 150. These steps are repeated with the other three nucleoside triphosphates to complete sequencing of all the DNA molecules on the pixels of the array. Alternatively, more than one type of nucleoside triphosphate modified with different moieties may be added to the solution 150. The electrodes 130A, 130T, 130G and 130C may detect that the next unpaired base thereon by detecting the rate of charge of discharge on these electrodes respectively, caused by redox reactions of the different moieties on the nucleoside triphosphate. Other DNA sequencing methods that can be applied to the array include those disclosed in U.S. patent application Ser. No. 11/967,600, titled "Electronic Sensing for Nucleic Acid Sequencing," filed Dec. 31, 2007, the disclosures of which are incorporated herein by reference in its entirety.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A device comprising:
 a plurality of first reaction electrodes arranged in an array, the plurality of first reaction electrodes configured to be exposed to a solution and having a capacitance;
 first circuitry configured to set a DC voltage on the plurality of first reaction electrodes, and configured to charge or discharge the capacitance through a redox reaction occurring at the plurality of first reaction electrodes; and
 second circuitry configured to measure a rate of charging or discharging of the capacitance of the plurality of first reaction electrodes.

2. The device of claim 1, wherein the second circuitry is configured to measure the rate of charging or discharging of the capacitance by measuring a voltage of the plurality of first reaction electrodes as a function of time.

3. The device of claim 1, wherein the second circuitry is configured to measure the rate of charging or discharging of the capacitance by measuring an amount of voltage change from a voltage of the bias source at a time point.

4. The device of claim 1, wherein the second circuitry is configured to measure the rate of charging or discharging of the capacitance by measuring an amount of time for a voltage of the plurality of first reaction electrodes to change from a voltage of the bias source by a predetermined amount.

5. A device comprising:
 a plurality of first reaction electrodes arranged in an array, the plurality of first reaction electrodes configured to be exposed to a solution and having a capacitance;
 first circuitry configured to controllably connect the plurality of first reaction electrodes to a bias source and controllably disconnect the plurality of first reaction electrodes from the bias source; and
 second circuitry configured to measure a rate of charging or discharging of the capacitance of the plurality of first reaction electrodes.

6. The device of claim 5, wherein the capacitance includes self-capacitance of the plurality of first reaction electrodes and capacitance of interfaces between the plurality of first reaction electrodes and the solution.

7. The device of claim 5, wherein the charging or discharging of the capacitance is caused by redox reactions in the solution.

8. The device of claim 5, further comprising a reference electrode with a fixed reduction potential to the solution.

9. The device of claim 8, wherein the reference electrode is selected from the group consisting of standard hydrogen electrode (SHE), normal hydrogen electrode (NHE), reversible hydrogen electrode (RHE), saturated calomel electrode (SCE), copper-copper(II) sulfate electrode (CSE), silver-silver chloride (Ag/AgCl) electrode, silver pseudoreference electrode, and quasi-reference (QRE).

10. The device of claim 8, further comprising a second reaction electrode configured to be electrically biased relative to the solution.

11. The device of claim 10, wherein the second reaction electrode is not consumed.

12. The device of claim 10, wherein the first reaction electrodes and/or the second reaction electrodes are coated with an organic or inorganic coating.

13. The device of claim 10, wherein the first reaction electrodes are selected from the group consisting of platinum, gold, indium tin oxide, diamond-like carbon doped with impurities, glassy carbon, silver, carbon nanotube, graphene, and conducting polymers; and/or
wherein the second reaction electrodes are selected from the group consisting of platinum, gold, indium tin oxide, diamond-like carbon doped with impurities, glassy carbon, silver, carbon nanotube, graphene, and conducting polymers.

14. The device of claim 5, wherein the plurality of first reaction electrodes are a material that is not consumed by the solution.

15. The device of claim 5, wherein the first circuitry comprises a switch.

16. The device of claim 5, wherein the second circuitry is configured to measure the rate of charging or discharging of the capacitance by measuring a voltage of the plurality of first reaction electrodes as a function of time.

17. The device of claim 16, wherein the second circuitry is configured to measure the voltage of the plurality of first reaction electrodes without discharging the capacitance.

18. The device of claim 5, wherein the second circuitry is configured to measure the rate of charging or discharging of the capacitance by measuring an amount of voltage change from a voltage of the bias source at a time point.

19. The device of claim 5, wherein the second circuitry is configured to measure the rate of charging or discharging of the capacitance by measuring an amount of time for a voltage of the plurality of first reaction electrodes to change from a voltage of the bias source by a predetermined amount.

20. The device of claim 5, wherein the device is a microchip.

21. The device of claim 5, wherein the second circuitry comprises a memory.

22. The device of claim 5, further comprising a multiplexer and a controller.

23. The device of claim 5, further comprising at least one second reaction electrode in vicinity of at least one of the plurality of first reaction electrodes.

24. The device of claim 5, wherein a geometric area of each of the first reaction electrodes is between 0.01 µm2 and 100 µm2.

25. The device of claim 5, where the plurality of first reaction electrodes comprises between 100 and 10,000,000,000 first reaction electrodes; and the first circuitry comprises a plurality of measurement circuits, each of which corresponding to one of the plurality of first reaction electrodes.

26. The device of claim 5, wherein the second circuitry is shared among more than one first electrodes in the plurality of first electrodes.

* * * * *